(12) United States Patent
Hoeppner et al.

(10) Patent No.: US 7,572,262 B1
(45) Date of Patent: Aug. 11, 2009

(54) FEMORAL GUIDE FOR REVISION SURGERY

(75) Inventors: Jacy C Hoeppner, Warsaw, IN (US); Michael Keating, Indianapolis, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 430 days.

(21) Appl. No.: 11/147,040

(22) Filed: Jun. 7, 2005

(51) Int. Cl.
A61B 17/58 (2006.01)
A61B 17/60 (2006.01)
A61F 2/00 (2006.01)

(52) U.S. Cl. .......................................... 606/88; 606/87

(58) Field of Classification Search ............ 606/86–89, 606/96; 83/821, 827, 829, 662
See application file for complete search history.

(56) References Cited

U.S. PATENT DOCUMENTS

| | | | | |
|---|---|---|---|---|
| 4,134,213 A * | 1/1979 | Kushmuk | ...................... | 33/512 |
| 4,574,794 A * | 3/1986 | Cooke et al. | .................. | 606/88 |
| 5,445,642 A | 8/1995 | McNulty et al. | | |
| 5,562,675 A | 10/1996 | McNulty et al. | | |
| 5,601,563 A * | 2/1997 | Burke et al. | ................... | 606/86 |
| 5,683,397 A * | 11/1997 | Vendrely et al. | .............. | 606/88 |
| 5,776,137 A | 7/1998 | Katz | | |
| 5,810,829 A * | 9/1998 | Elliott et al. | .................. | 606/80 |
| 6,024,746 A | 2/2000 | Katz | | |
| 6,059,788 A | 5/2000 | Katz | | |
| 6,077,270 A | 6/2000 | Katz | | |
| 6,080,196 A | 6/2000 | Bertin | | |
| 6,096,043 A * | 8/2000 | Techiera et al. | ............... | 606/88 |
| 6,226,881 B1 * | 5/2001 | Landauer | ..................... | 33/515 |
| 6,575,980 B1 * | 6/2003 | Robie et al. | ................... | 606/88 |
| 6,673,077 B1 | 1/2004 | Katz | | |
| 6,740,092 B2 * | 5/2004 | Lombardo et al. | ............ | 606/88 |
| 7,182,737 B2 * | 2/2007 | Kim et al. | .................... | 600/590 |
| 2004/0039395 A1 | 2/2004 | Coon et al. | | |
| 2004/0039398 A1 | 2/2004 | Cortellessa et al. | | |
| 2004/0153066 A1 | 8/2004 | Coon et al. | | |
| 2006/0122617 A1 * | 6/2006 | Lavallee et al. | ............... | 606/87 |

OTHER PUBLICATIONS

"T1 Revision Instruments Surgical Technique" brochure, copyright 1999, Biomet, Inc.

* cited by examiner

Primary Examiner—Eduardo C Robert
Assistant Examiner—Andrew Yang
(74) Attorney, Agent, or Firm—Harness, Dickey

(57) ABSTRACT

A femoral guide for use in implanting a knee prosthesis. The femoral guide includes a cutting guide, and a referencing guide coupled to the cutting guide and adapted for locating a femoral joint line.

5 Claims, 2 Drawing Sheets

FEMORAL GUIDE FOR REVISION SURGERY

INTRODUCTION

Malposition of the joint line is a common complication of primary and especially revision knee surgery. Various known instruments can be used to reference the natural joint line of the average knee using approximate referencing landmarks. These landmarks include, for example, the inferior pole of the patella, the fibular head, and the epicondyles.

Although the existing instruments and guides can be satisfactory for their intended purposes, there is still a need for versatile referencing guides in revision surgery

SUMMARY

The present teachings provide a femoral guide for use in implanting a knee prosthesis. The femoral guide includes a cutting guide, and a referencing guide coupled to the cutting guide for locating a femoral joint line.

The present teachings also provide a method for resecting the distal femur to implant a knee prosthesis. The method includes referencing the medial and lateral epicondyles, locating the femoral joint line, securing a cutting guide to the distal femur, and resecting at least a portion of the distal femur.

The present teachings provide a femoral guide for use in implanting a knee prosthesis. The femoral guide includes a cutting guide for resecting at least a portion of the distal femur, the cutting guide including a guiding surface, and a referencing guide coupled to the cutting guide. The referencing guide includes medial and lateral arms that extend to anatomically predetermined distances from the guiding surface to corresponding medial and lateral epicondyles of the femur for locating a femoral joint line.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. For example, although the present teachings are illustrated for specific resections in revision knee surgeries, the present teachings can be used for primary knee surgeries, and for femoral resections including, but not limited to, box, anterior, posterior and chamfer resections.

Figure 1:
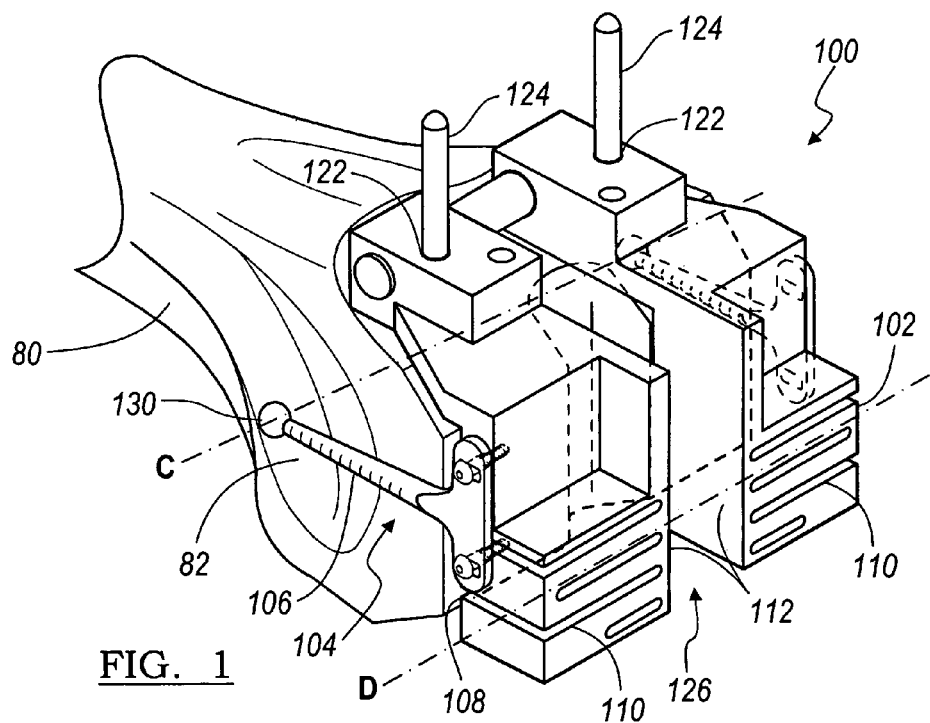
FIG. 1 is a perspective environmental view of a femoral guide according to the present teachings, the femoral guide shown on a distal femur.
Figure 2:
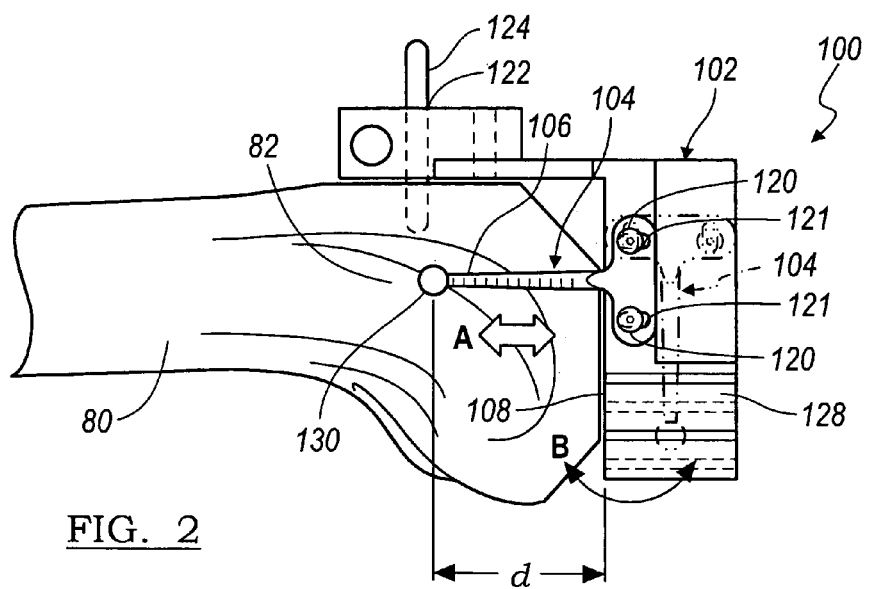
FIG. 2 is an elevated side view of a femoral guide according to the present teachings, the femoral guide shown on a distal femur.
Figure 3:
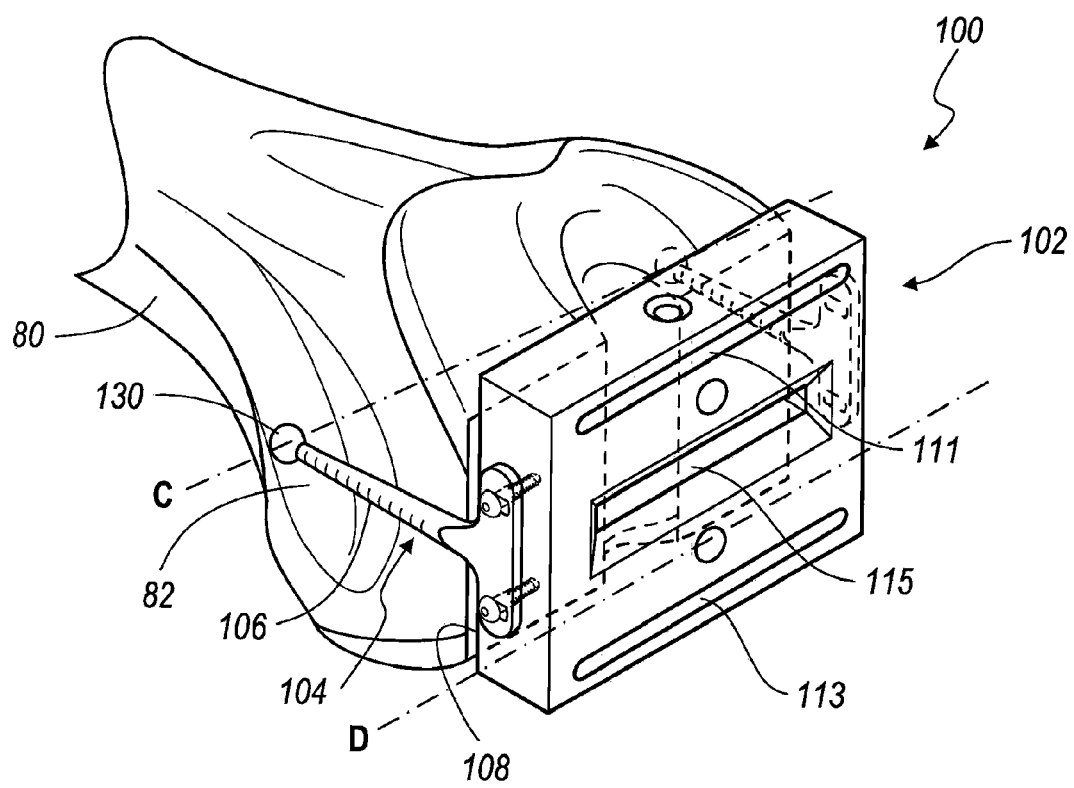
FIG. 3 is a perspective environmental view of a femoral guide according to the present teachings, the femoral guide shown on a distal femur.

Referring to FIGS. 1-3, an exemplary femoral guide 100 according to the present teachings includes a cutting guide 102 and a referencing guide 104 integrally or modularly coupled to the cutting guide 102 by known means, such as fasteners, quick connectors, or other connectors 120.

The cutting guide 102 can be, for example, a known box resection guide for assisting in intercondylar box resection and other distal femur cuts, as illustrated in FIG. 1, or a four-in-one cutting guide for posterior, anterior and chamfer cuts, as illustrated in FIG. 3, or any other femoral cutting guide with or without anterior and/or posterior flanges. The cutting guide 102 can include structural features for performing the appropriate resections, such as, for example, various saw blade slots 110 for distal cuts, and openings 122 for receiving drill bits or bone pins/nails 124. The cutting guide 102 can also include two opposing surfaces 112 defining a channel 126 for receiving a femoral box chisel or other cutting tool, as illustrated in FIG. 1. Referring to FIG. 3, the cutting guide 102 can include an anterior slot 111, a posterior slot 113, and chamfer slots 115 for corresponding anterior, posterior and chamfer cuts in primary surgery. The cutting guide 102 can include a guiding surface 108 which is bought in proximity to the distal femur 80 when the cutting guide 102 is secured thereon, as shown in FIG. 2. The distal femur 80 can be fully resected, as illustrated in FIG. 1 when used in a revision procedure, or partially resected, as illustrated in FIG. 3, when used in a primary procedure.

The referencing guide 104 can be adapted for referencing the medial and lateral epicondyles 82 of the femur for establishing the location of the natural joint line D. Establishing the natural joint line D allows the surgeon to select the size and location of the components of the knee prosthesis to replicate natural (anatomic) or optimal knee motion. The referencing guide 104 can include, for example, lateral and medial arms or styli 106 that extend proximally from corresponding sides 128 of the cutting guide 102 toward the distal femur 80. The medial and lateral arms 106 can include engagement tips 130 and can be dimensioned such that when the tips 130 are engaged to the corresponding epicondyles 82, the arms 106 position the guiding surface 108 to define substantially the location of the natural joint line D. Distances "d" between each tip 130 and the guiding surface 108 can be selected for the anatomy of an average knee, and can also be adjustable for variations therefrom. For example, the distance d for the medial arm 106 can be about 3 cm and for the lateral arm 106 about 2.5 cm, but adjustability within a few millimeters above and below the average in the proximal-distal direction can be provided, as discussed below. Referring to FIG. 1, it is noted that axis C passing through the medial and lateral epicondyles is not parallel to the natural joint line D.

The arms 106 can be integrally or modularly connected to the cutting guide 102. The arms 106 can also be movably and or adjustably connected to the cutting guide 102, such that the distance d of each arm 106 can be separately adjusted, as desired by the surgeon in a particular application. The arms 106 can be, for example, separately slidable or adjustable in the distal-proximal direction A using fasteners 120 that can be secured in elongated slots 121. The fasteners 120 can also be pivotable in the direction of curved arrows B about a mediolateral axis, such that arms 106 can be stored compactly, when the femoral guide 100 is not in use, and then pivoted back to an engagement position illustrated in FIG. 2 for use. The arms 106 can also be separately and completely removable from the femoral guide 100. Further, adjustability in the anterior-posterior and lateral-medial direction can also be provided by known means, including using arms 106 that are slidable in those directions, such that anatomic variations from the average knee can be accommodated.

In operation, the joint line D can be established by placing the femoral guide 100 at the distal femur 80 and adjusting the location of the guiding surface 108 by adjusting the length and location of the medial and lateral arms 106 as described above, such that the tips 130 of the medial and lateral arms 106 are approximately at the corresponding epicondyles 82 within a selected tolerance, such as, for example, about 2 mm or less. The femoral guide 100 can be secured in this position and the femoral box can be prepared by using known cutting instrumentation, such as, for example, a femoral box chisel through the channel 126 and/or other saw blades through the distal slots 110, as shown in FIG. 1, or through the anterior slot 111, posterior slot 113, and chamfer slots 115, as shown in FIG. 3. Although in a revision procedure the distal condyles of the femur 80 may be already resected, in primary surgery the cutting guide 102 can be a distal femur resection guide adapted for resecting the condyles instead or in addition to resecting the femoral box.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method for resecting a distal femur to implant a knee prosthesis, the method comprising:
   securing a cutting guide to the distal femur;
   aligning a substantially planar guiding surface of the cutting guide substantially parallel to a resected distal surface of the distal femur;
   pivoting first and second referencing arms extending from the cutting guide from a storage position in which the first and second referencing arms are substantially parallel to the guiding surface to an engagement position in which the first and second referencing arms are substantially perpendicular to the guiding surface, the first referencing arm having a first length extending from a first proximal end coupled to the cutting guide to a first distal engagement tip, the second referencing arm having a second length extending from a second proximal end coupled to the cutting guide to a second distal engagement tip;
   engaging the first and second engagement tips of the corresponding first and second referencing arms to medial and lateral epicondyles of the distal femur;
   referencing the medial and lateral epicondyles along a line passing through the first and second engagement tips;
   locating a natural femoral joint line on the guiding surface by pre-selecting the first and second lengths to correspond to first and second distances from the first and second epicondyles to the natural femoral joint line along the first and second referencing arms; and
   resecting at least a portion of the distal femur through a cutting slot passing though the guiding surface.

2. The method of claim 1, wherein the first and second referencing arms have fixed and unequal lengths.

3. The method of claim 1, wherein resecting the distal femur comprises cutting a portion of the distal femur.

4. The method of claim 3, wherein cutting a portion of the distal femur comprises making an anterior cut, or posterior cut, or chamfer cut, or box cut, or combinations thereof.

5. The method of claim 1, further comprising adjusting the length of the first and second referencing arms in a distal-proximal direction substantially perpendicular to the guiding surface.

* * * * *